US011419485B2

(12) United States Patent
Wieters

(10) Patent No.: US 11,419,485 B2
(45) Date of Patent: Aug. 23, 2022

(54) STEREOSCOPIC OPTICAL SYSTEM OF A SURGICAL INSTRUMENT AND METHOD FOR PRODUCING SAME

(71) Applicant: OLYMPUS WINTER & IBE GMBH, Hamburg (DE)

(72) Inventor: Martin Wieters, Barsbuettel (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 466 days.

(21) Appl. No.: 16/583,849

(22) Filed: Sep. 26, 2019

(65) Prior Publication Data
US 2020/0022568 A1    Jan. 23, 2020

Related U.S. Application Data

(63) Continuation of application No. PCT/EP2018/057351, filed on Mar. 22, 2018.

(30) Foreign Application Priority Data

Apr. 6, 2017 (DE) .................... 10 2017 107 414.7

(51) Int. Cl.
*A61B 1/00*    (2006.01)
*G02B 30/25*    (2020.01)
(Continued)

(52) U.S. Cl.
CPC ...... *A61B 1/00193* (2013.01); *A61B 1/00096* (2013.01); *G02B 23/2415* (2013.01);
(Continued)

(58) Field of Classification Search
CPC ............ A61B 1/00193; A61B 1/00096; A61B 1/0008; G02B 23/2415; G02B 30/25;
(Continued)

(56) References Cited

U.S. PATENT DOCUMENTS

2015/0282692 A1* 10/2015 Wieters .................... H01F 7/126
  604/95.05
2015/0340937 A1* 11/2015 Wieters ................. H01F 7/1615
  310/17
2015/0340939 A1* 11/2015 Kelp ........................ H01F 7/122
  310/12.19

FOREIGN PATENT DOCUMENTS

DE    10 2014 103 169 A1    9/2015
DE    10 2014 204 736 A1    9/2015
(Continued)

OTHER PUBLICATIONS

International Search Report dated Jun. 8, 2018 received in PCT/EP2018/057351.

*Primary Examiner* — Alexandra L Newton
(74) *Attorney, Agent, or Firm* — Scully, Scott, Murphy & Presser, P.C.

(57) ABSTRACT

A stereoscopic optical system including: left and right channels; an electromagnetic actuator including a stator and rotor; wherein first optical components of the left channel are arranged in a left tube and second optical components of the right channel are arranged in a right tube; the stator is arranged outside the guide tubes; the rotor includes a left rotor, in which one or more of the first optical components is accommodated, and a right rotor, in which one or more of the second optical components is accommodated; the left and right rotors are mounted in one of the left and right tubes to be movable in a longitudinal axial direction; the left and right rotors include paramagnetic and/or ferromagnetic material and are movable by an electromagnetic field; the stator includes distal and proximal permanent magnets oppositely polarized; and the stator includes an electric coil for generating the electromagnet field.

13 Claims, 7 Drawing Sheets

(51) Int. Cl.
*G02B 23/24* (2006.01)
*H01F 7/16* (2006.01)
*H02K 33/18* (2006.01)

(52) U.S. Cl.
CPC ............ *G02B 30/25* (2020.01); *H01F 7/1615* (2013.01); *H02K 33/18* (2013.01)

(58) Field of Classification Search
CPC .......... G02B 7/06; G02B 7/08; G02B 23/243; H01F 7/1615; H02K 33/18; F03G 7/0665
See application file for complete search history.

(56) References Cited

FOREIGN PATENT DOCUMENTS

| | | | |
|---|---|---|---|
| DE | 102014103169 A1 * | 9/2015 | ......... G02B 23/2415 |
| EP | 2 947 756 A2 | 11/2015 | |
| WO | 2016/012248 A1 | 1/2016 | |

* cited by examiner

STEREOSCOPIC OPTICAL SYSTEM OF A SURGICAL INSTRUMENT AND METHOD FOR PRODUCING SAME

CROSS-REFERENCE TO RELATED APPLICATION

The present application is a continuation of PCT/EP2018/057351 filed on Mar. 22, 2018, which is based upon and claims the benefit to DE 10 2017 107 414.7 filed on Apr. 6, 2017, the entire contents of each of which are incorporated herein by reference.

BACKGROUND

Field

The present disclosure relates to a stereoscopic optical system of a surgical instrument, comprising a left optical channel, a right optical channel and an electromagnetic actuator with a stator and a rotor. The present disclosure further relates to a surgical instrument as well as a method for producing a stereoscopic optical system of a surgical instrument, having a left optical channel, a right optical channel and an electromagnetic actuator with a stator and a rotor.

Prior Art

Electromagnetic actuators have many and varied applications. For example, switches can be operated, or micro-optics set or adjusted, with them. In the case of surgical instruments, for example endoscopes, these compact-design actuators can be used in order to alter a focus or a magnification of an optical system. In the case of endoscopes having a variable viewing direction, it is in addition possible to set or alter a viewing direction of the optical system with the aid of an electromagnetic actuator. The optical characteristics of an optical system are altered by moving an optical component, for example a lens, a prism or an aperture by means of the actuator, wherein the optical component is located in or on the rotor of the actuator.

Bistable and monostable electromagnetic actuators are known. In the case of a bistable electromagnetic actuator, a rotor is provided, which is held in a permanent magnetic field in one of two extreme positions (end positions) and, by switching an electromagnetic field, can be transferred from one of these two stable positions into the other stable position respectively. In the case of a monostable electromagnetic actuator, the rotor is held stably in its resting position by a magnetic field which is generated by one or more permanent magnets. As a result of applying an electromagnetic field generated by a magnetic coil, the rotor is moved out of said stable resting position. Bistable systems are suitable for two-stage operation with end positions which are maintained without power. On the other hand, monostable systems are suitable for continual adjustment.

As already indicated, electromagnetic actuators can be deployed in order to set or adjust an optical system of a surgical instrument. The optical system of a stereo endoscope comprises two lenses which are ideally set or focused simultaneously with one another. To this end, it would be possible to deploy two separate electromagnetic actuators as would otherwise be deployed to adjust individual optics. However, this is associated with high costs. In addition, it is desirable if the optical axes of the two lenses, which are deployed for the stereoscopic imaging, observe the largest possible distance, the so-called stereo distance, from one another. A large stereo distance makes a good 3D effect possible. At the same time, luminous optics are desirable such that, if possible, lenses having as large a diameter as possible are to be used. The larger the optical elements become, the smaller the available distance between the lenses. If the stereo distance is to be kept constant, the diameter of a tube surrounding the two lenses increases. In addition, the electromagnetic actuators have to be accommodated. The requirements indicated are therefore more or less in direct contradiction to the restricted installation space present in the tube of the endoscope.

SUMMARY

It is an object to provide a stereoscopic optical system, a surgical instrument having a stereoscopic optical system as well as a method for producing a stereoscopic optical system, which is improved with respect to the prior art, for example, has a compact design.

Such object can be achieved by a stereoscopic optical system of a surgical instrument, comprising a left optical channel, a right optical channel and an electromagnetic actuator with a stator and a rotor, wherein the optical components of the left optical channel are arranged in a left guide tube and optical components of the right optical channel are arranged in a separate right guide tube, wherein the stator is arranged outside the guide tubes and the rotor comprises a left rotor, in which at least one optical component of the left optical channel is accommodated, and a right rotor, in which at least one optical component of the right optical channel is accommodated, and wherein the left and the right rotor are mounted in the respective guide tube such that they can move in a longitudinal axial direction of the left and right guide tube, wherein the rotors each at least partially comprise a paramagnetic and/or ferromagnetic material and can be moved in the longitudinal axial direction by application of an electromagnetic field, wherein the stator comprises a distal permanent magnet and a proximal permanent magnet which are oppositely polarized in the longitudinal axial direction, and wherein the stator comprises an electric coil for generating the electromagnetic field.

The left and the right guide tube can be aligned parallel to one another, which means that a longitudinal axial direction of the left guide tube can be oriented parallel to a longitudinal axial direction of the right guide tube. If it is not necessary to distinguish between the left and the right guide tube, reference is also made below in general to a longitudinal axial direction which can be oriented in the same direction as the longitudinal axial directions of the left and right guide tube. It is also provided that the left and the right guide tube can enclose an angle of, for example, 2°. This angle between the longitudinal axial direction of the left guide tube and the longitudinal axial direction of the right guide tube can be less than 5°. If reference is purely made to a longitudinal axial direction and the left and the right guide tube enclose an angle, said longitudinal axial direction can be located in the center between the longitudinal axial direction of the left guide tube and the longitudinal axial direction of the right guide tube.

In the stereoscopic optical system the right rotor and the left rotor can be operated with the aid of a single and joint electromagnetic actuator. It can be technically simple and, in addition, can be inexpensive to realize such a construction. In addition, said construction can only take up a very small installation space.

Since separate guide tubes for the left optical channel and the right optical channel can be provided, a joint holder can be provided for both optical channels or respectively for the optical components thereof. Such a holder can be secured or respectively fixed with respect to rotation about its longitudinal axial direction to avoid a subsequent twisting of the optics with respect to the remaining optical components of the stereoscopic optical system, for example of the image sensors. Such rotation can be possible, for example, by deploying a key, in which, for example, a clearance fit can be used in order to make possible the desired axial movability. In another variation, a holder having an oval cross-section can be used where the holder slides in a suitable oval bore of a sliding tube. However, such a construction would require an oval cross-section which may be more expensive to manufacture and may be less precise.

A separate guide tube can also be provided for each of the left rotor and the right rotor. The guide tubes can have a circular cross-section.

According to an embodiment, a distal end of the stator can be formed by a distal stator pole shoe and an opposite proximal end in the longitudinal axial direction can be formed by a proximal stator pole shoe. Furthermore, the stator can comprise a central stator pole shoe which is arranged between the permanent magnets in the longitudinal axial direction. The central stator pole shoe can be formed from a proximal central stator part pole shoe and from a distal central stator part pole shoe. An air gap can be provided between the distal central stator part pole shoe and the proximal central stator part pole shoe.

The coil can comprise a distal coil and a proximal coil, wherein the distal stator pole shoe, a distal coil, the distal permanent magnet and the distal central stator part pole shoe can form a prefabricated distal assembly and the proximal central stator part pole shoe, a proximal coil, the proximal permanent magnet and the proximal stator pole shoe can form a prefabricated proximal assembly, wherein the components of the distal and/or the proximal assembly can be bonded to one another.

Using stator pole shoes can increase the efficiency of the electromagnetic actuator thanks to an improved magnetic flow guidance. As a result, larger retention forces can be provided or lower control currents can be deployed.

The central stator pole shoe can be thicker than the outer stator pole shoes, i.e. the distal stator pole shoe or the proximal stator pole shoe. For example, the central stator pole shoe can have a material thickness, measured in the longitudinal axial direction, which is 1.2-times to double the size of the material thickness of the outer pole shoes measured in the same direction.

The air gap between the distal central stator part pole shoe and the proximal central stator part pole shoe can form a distal and a proximal assembly which are not mechanically connected to one another. Since the permanent magnets of the two assemblies repel one another due to their oppositely polarized orientation, the two assemblies can be aligned autonomously and independently of any existing component tolerances with a distal and a proximal stop. The use of an adhesive for connecting the two assemblies can be dispensed with. If a mechanical connection of the two assemblies is to be produced, an adhesive can be deployed, which can have a low volume shrinkage during curing. For example, an adhesive which loses less than 5% volume during curing can be used.

The distal assembly and the proximal assembly can have an identical construction to one another. In order to realize the opposite magnetic orientation of the permanent magnets in the electromagnetic actuator, either the proximal assembly or the distal assembly can be installed, rotated by 180° with respect to the other assembly in each case during erection. The assemblies can be wired appropriately such that they generate magnetic fields having the same orientation. Using prefabricated assemblies can accelerate the production of the electromagnetic actuator.

According to a further embodiment, the left and the right guide tube can be accommodated in a joint component which has a dumbbell-shaped cross-section in a plane transversely to the longitudinal axial direction, and wherein an inner contour of the pole shoes can correspond to an outer contour of the dumbbell-shaped component and an outer contour of the pole shoes can be in the form of a circular segment, at least in sections.

The two optical channels, i.e. the two guide tubes, can be accommodated in a joint component or can be provided by such a component. In order to achieve a high efficiency of the actuator, the stator pole shoes can be located as close as possible to the rotor. For example, the stator pole shoes can have a geometry, into which two bores are introduced in order to receive the respective receiving tubes. However, such a construction can result in a very narrow crosspiece between the two bores, with the corresponding mechanical instabilities. The central component, in which the two receiving tubes are accommodated, can be in the shape of a dumbbell. The stator pole shoes can reach up to the outer surface of said dumbbell-shaped component. Thus, a huge mechanical stability can be achieved, on the one hand, which can simplify the assembly of the system. At the same time, the stator pole shoes can be positioned sufficiently close to the rotors such that an efficient magnetic flow guidance can be provided.

It is additionally provided that the stator pole shoes can extend in a radial direction perpendicular to the longitudinal axial direction from an outer side of the dumbbell-shaped component up to an outer side of the permanent magnets facing away from the dumbbell-shaped component and/or up to an outer side of the magnetic coils facing away from the dumbbell-shaped component. The flow guidance can be improved by such a configuration.

According to a further embodiment, the coil can comprise a distal coil and a proximal coil, wherein the two coils can extend in the longitudinal axial direction on both sides of the central stator pole shoe and can be electrically coupled to one another such that the distal coil generates a first magnetic field which is oriented similarly to a second magnetic field generated by the proximal coil. Thanks to the division of the magnetic coil into a first coil and a second coil, said magnetic coil can be integrated into the prefabricated proximal assembly and the prefabricated distal assembly.

In a further embodiment, the coil can surround the left and the right guide tube and can be oval in a plane arranged perpendicular to the longitudinal axial direction. The coil can have the form of two semi-circular segments, with straight pieces being inserted in each case between the ends of said semi-circular segments located on one side. In other words, the form of the coil can correspond, for example, to the form of a track. Creating such a geometry of the coil can require an acceptable outlay, but allows the magnetic flow to be coupled efficiently into the crucial regions of the electromagnetic actuator. The form of the coil can be adapted to an outer contour of the guide tubes. Individual coils can be used for each optical channel. However, an oval coil, which acts jointly for both guide tubes, can be less expensive and, in addition, can be a space-saving solution.

According to a further embodiment, the permanent magnets can be arranged on an outer side of the coil facing away from the guide tubes. Such a design can be compact since an external magnetic return element can be dispensed with. The permanent magnets can act as magnetic return elements, at least in regions.

It is additionally provided that the permanent magnets can be block-shaped magnets which can be arranged in two groups, wherein the groups can be arranged opposite one another on a flat side each of an arrangement formed from the left and right guide tube. Installation space can be provided on the flat sides of the guide tubes located next to one another since the endoscope tube, in which the unit is accommodated, can have a circular inside diameter. The optics of the right and left channel can be positioned as far as possible from one another in order to thus realize a large stereo base. The block-shaped permanent magnets can be accommodated in the remaining installation space.

On the flat sides of the tubes located next to one another, available installation space can be provided with a circular receiving opening. Said flat sides can be located at least approximately parallel to a distance of the two tubes. However, no available installation space exists on the front sides which can be located perpendicularly to said flat sides, that is to say in a plane at least approximately perpendicular to the distance between the two tubes, since the two tubes can be placed next to one another in the circular receiving opening with as large a distance as possible. Since the coils may be wound with a uniform wall thickness, it may not be possible to save on the material of the coils on said front sides of the arrangement. The material of the stator and the material of the permanent magnets can, however, be dispensed with on the front sides. The flat sides can be utilized in order to house the permanent magnets. Magnetic disks can be used which can have a very thin wall thickness, at least in sections. Since magnetic material can be brittle, the handling of such magnetic disks can be very difficult during the erection of the stereoscopic optical system. Magnetic blocks can be, on the other hand, stable and, in addition, simple and inexpensive to produce. Additionally, the arrangement of the magnets in the indicated region can bring about a compensation of the magnetic flow guidance influenced by the form of the stator pole shoes.

According to a further embodiment, the permanent magnets can form magnetic return elements for the magnetic field generated by the electric coil. Thus, separate magnetic return elements can be avoided, which can decrease the design of the electromagnetic actuator.

According to a further embodiment, at least one of the permanent magnets can comprise magnetically hard particles which can be embedded in a plastic matrix, wherein said permanent magnet can be produced using an injection molding method and at least one coil wire of the coil can be molded in at least one permanent magnet. For example, NdFeB particles (neodymium iron boron) or a mixture of said materials, which can be stirred into an epoxy resin adhesive, is/are suitable as magnetic particles. In order to produce the permanent magnets, a cavity between the stator pole shoes can be emptied. Said cavity can be subsequently occupied by the permanent magnet thus produced. During said operation not only can the permanent magnet itself be produced, but the parts of the assemblies can also be connected or respectively molded together. It is for example provided that the assembly thus produced can be subsequently magnetized such that the magnetic particles assume the desired magnetic orientation.

Such object can in addition be achieved by a surgical instrument, such as an endoscope, having a stereoscopic optical system according to one or more of the embodiments indicated above.

The surgical instrument can be produced economically and efficiently. In addition, a large stereo base can be realized in such a system, such as for use with the imaging characteristics of a surgical instrument, such as an endoscope. Moreover, the same or similar advantages apply to the surgical instrument as have already been mentioned with respect to the stereoscopic optical system itself such that repetitions shall be dispensed with.

Such object can be, in addition, achieved by a method for producing a stereoscopic optical system of a surgical instrument, having a left optical channel, a right optical channel and an electromagnetic actuator with a stator and a rotor, characterized in that optical components of the left optical channel are arranged in a left guide tube and optical components of the right optical channel are arranged in a separate right guide tube, wherein the stator is arranged outside the guide tubes and the rotor comprises a left rotor, in which at least one optical component of the left optical channel is accommodated, and a right rotor, in which at least one optical component of the right optical channel is accommodated, and wherein the left and the right rotor are mounted in the respective guide tube such that they can move in a longitudinal axial direction of the left and right guide tube, wherein the rotors each at least partially comprise a paramagnetic and/or ferromagnetic material and can be moved in the longitudinal axial direction by application of an electromagnetic field, wherein a distal permanent magnet and a proximal permanent magnet are arranged in the stator in such a way that they are oppositely polarized in the longitudinal axial direction, and wherein an electric coil for generating the electromagnet field is arranged in the stator.

The same or similar advantages also apply to the method for producing a stereoscopic optical system as have already been mentioned with respect to the stereoscopic optical system itself.

According to an embodiment, a distal end of the stator can be formed by a distal stator pole shoe and an opposite proximal end in the longitudinal axial direction can be formed by a proximal stator pole shoe, and the stator can comprise a central stator pole shoe which can be arranged between the permanent magnets in the longitudinal axial direction and can be formed from a proximal central stator part pole shoe and from a distal central stator part pole shoe, wherein a distal assembly is prefabricated in that the distal stator pole shoe, a distal coil, the distal permanent magnet and the distal central stator part pole shoe can be bonded to one another and a proximal assembly can be prefabricated in that the proximal central stator part pole shoe, a proximal coil, the proximal permanent magnet and the proximal stator pole shoe can be bonded to one another.

The permanent magnets can be block-shaped magnets, wherein the magnets can be arranged in two groups and the groups can be arranged opposite one another on a flat side each of an arrangement formed from the left and right guide tube.

At least one of the permanent magnets can be produced in that magnetically hard particles can be embedded in a plastic matrix, wherein said permanent magnet can be produced using an injection molding method and at least one coil wire of the coil can be molded in at least one permanent magnet.

Further features will become evident from the description of embodiments, together with the claims and the appended drawings. Embodiments can fulfill individual features or a combination of several features.

BRIEF DESCRIPTION OF THE DRAWINGS

The embodiments are described below without limiting the general concept of the invention by means of exemplary embodiments with reference to the drawings, wherein reference is expressly made to the drawings regarding all of the details which are not explained in greater detail in the text, wherein.

In the drawings, the same or similar elements and/or parts are, in each case, provided with the same reference numerals such that they are not introduced again in each case.

DETAILED DESCRIPTION

Figure 1:
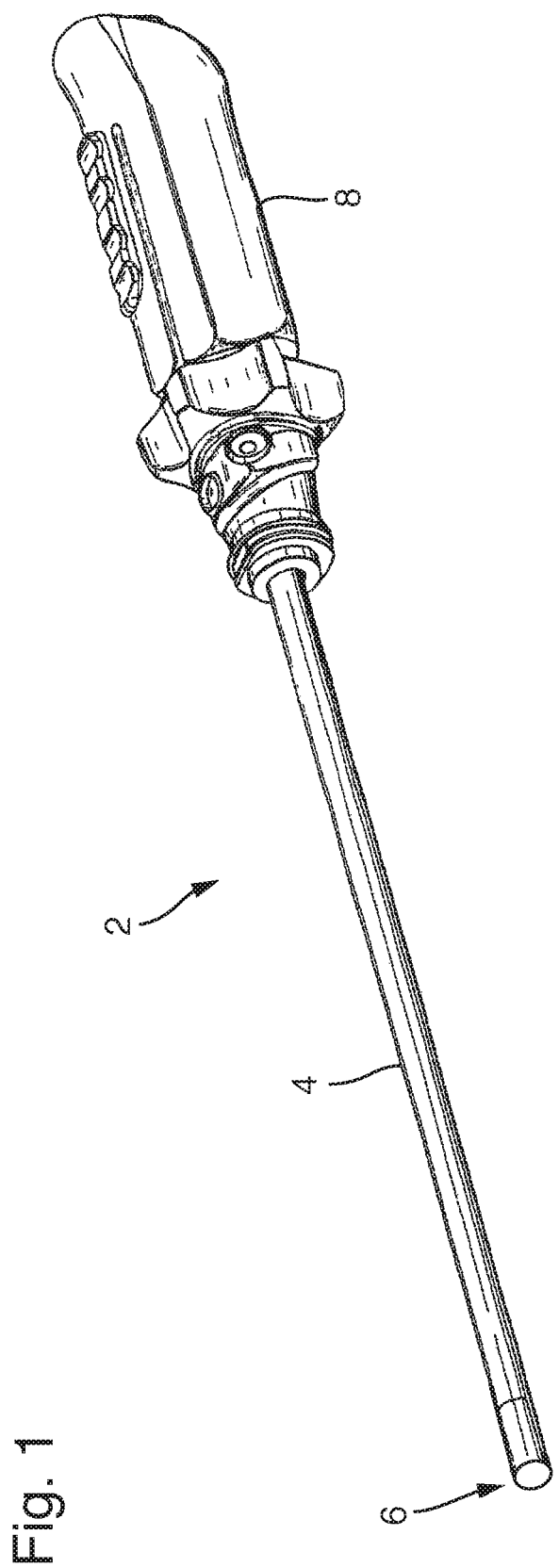
FIG. 1 illustrates an endoscope as an exemplary surgical instrument in a schematically simplified perspective view.

FIG. 1 shows an endoscope 2 as an exemplary surgical instrument in a schematically simplified perspective view. The endoscope 2 comprises an endoscope shaft (or insertion section) 4, in which an optical system is arranged, with which an operation or observation field lying in front of a distal end 6 of the endoscope shaft 4 is imaged. A handle 8 is located on a proximal end of the endoscope 2. The optical system (not represented in FIG. 1) arranged in the endoscope shaft 4 comprises an electromagnetic actuator.

Figure 2:
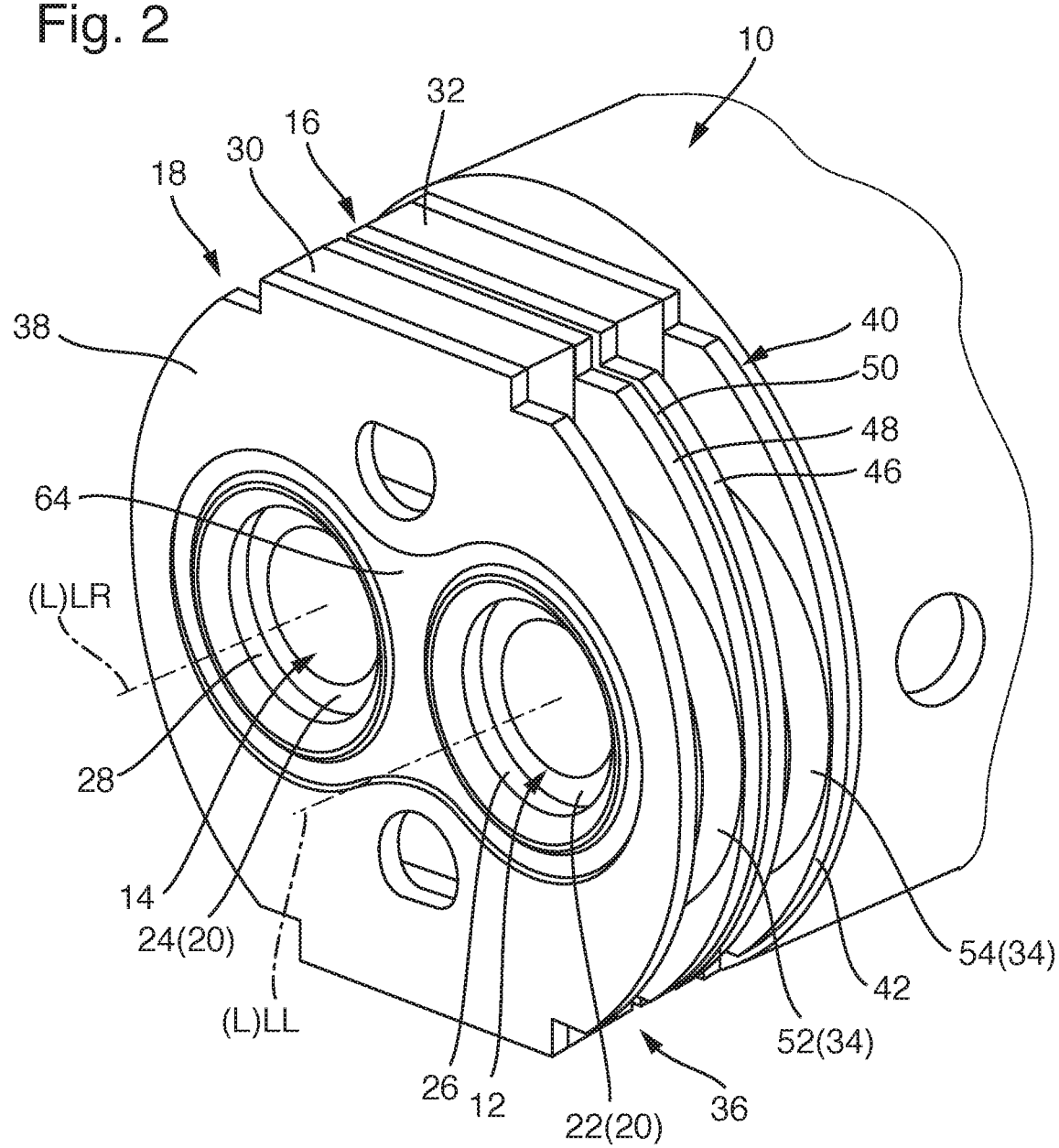
FIG. 2 illustrates a stereoscopic optical system in a schematically simplified perspective view.

FIG. 2 shows an exemplary optical system 10, as it can be provided in the distal end 6 of the endoscope shaft 4 of the endoscope 2. The optical system 10 is a stereoscopic system, as shown by the view which is represented in a schematic, simplified and perspective manner in FIG. 2.

FIG. 2 shows an installation situation, in which an endoscope tube which normally surrounds the stereoscopic optical system 10 is omitted, in order to expose the view of the components of the system. The stereoscopic optical system 10 comprises a left optical channel 12 and a right optical channel 14. The respective front lenses of the optical channels 12, 14 of the optical components of the left optical channel 12 and of the right optical channel 14 are represented, by way of example, in FIG. 2. The stereoscopic optical system 10 additionally comprises an electromagnetic actuator 16, comprising a stator 18 and a rotor 20. The optical components of the left optical channel 12, for example the front lens which is visible in FIG. 2, is/are accommodated in a left guide tube 26. This relates to at least a part of the optical components of the left optical channel 12. Optical components of the right optical channel 14 are arranged in a separate right guide tube 28 to the left guide tube 26. The two guide tubes 26, 28 are, for example, arranged parallel to one another. It is, however, likewise provided that the guide tubes 26, 28 are arranged at an angle of, for example, 2° to one another, wherein said angle does not as a general rule exceed 5°. Like the optical components of the left optical channel, the optical components of the right optical channel 14 are also at least partially arranged in the right guide tube 28. The guide tubes 26, 28 are, for example, separate components, for example tubes. It is likewise provided that the guide tubes 26, 28 are not separate components and, instead, are provided by bores inset in a dumbbell-shaped component 64.

The stator 18 is arranged outside the guide tubes 26, 28 and encloses the guide tubes 26, 28 completely. This applies to a direction perpendicular to a longitudinal axial direction of the guide tubes 26, 28. It is not necessary for the stator 18 to completely enclose the guide tubes 26, 28 in a longitudinal axial direction L.

The rotor 20 comprises a left rotor 22, in which at least one optical component of the left optical channel 12 is accommodated. The rotor 20 additionally comprises a right rotor 24, in which at least one optical component of the right optical channel 14 is accommodated. In the represented exemplary embodiment, the front lenses of the optical channels 12, 14 are each accommodated in the corresponding rotors 22, 24.

The left rotor 22 is mounted such that it can move in a left longitudinal axial direction LL along the left guide tube 26. The right rotor 24 is mounted in the right guide tube 28 such that it can move along a right longitudinal axial direction LR. The left longitudinal axial direction LL and the right longitudinal axial direction LR (each indicated with a dot-dashed line) are aligned parallel to one another. They coincide with the central longitudinal axes of the respective guide tubes 26, 28. If it is not necessary to distinguish between the left longitudinal axial direction LL and the right longitudinal axial direction LR below, reference is made in general to a longitudinal axial direction L which extends parallel to the left and the right longitudinal axial direction LL, LR.

The left rotor 22 and the right rotor 24 each at least partially comprise a paramagnetic and/or ferromagnetic material. In other words, the rotors 22, 24 are therefore at least partially produced from a paramagnetic and/or a ferromagnetic material. Thus, it is possible to move the rotors 22, 24 in the associated guide tube 26, 28 in the respective longitudinal axial direction LL, LR by application of an electromagnetic field 68. The stator 18 comprises a distal permanent magnet 30 and a proximal permanent magnet 32. The two permanent magnets 30, 32 are oppositely polarized in the longitudinal axial direction L. Further details regarding this are explained below in connection with FIGS. 6 and 7.

The stator 18 additionally comprises an electric coil for generating the electromagnetic field 68. Said coil is only partially visible in FIG. 2. The electromagnetic field 68 generated by it serves to move the rotors 22, 24 in their guide tubes 26, 28 along the respective longitudinal axial direction LL, LR.

Figure 3:
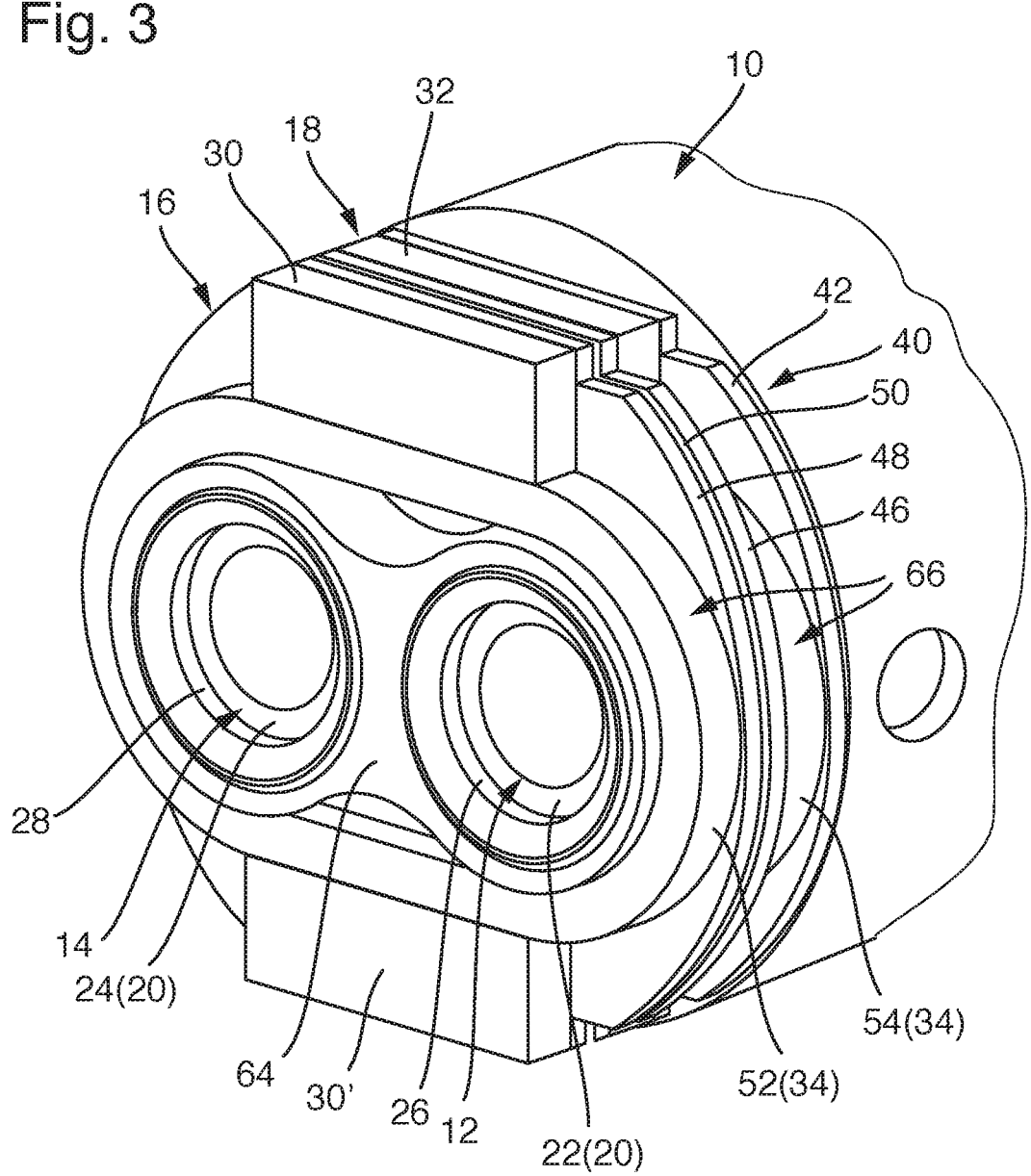
FIG. 3 illustrates said system, wherein a proximal stator pole shoe is removed, in order to expose the view of the components located behind it, FIG. 4 show illustrates s a stereoscopic optical system in a schematically simplified sectional view in a plane, in which a connecting line of the two optical channels is located.

FIG. 3 shows the stereoscopic optical system 10 of FIG. 2, likewise in a simplified perspective view, and in an installation situation at a distal end 6 of an endoscope shaft 4. In order to expose the view of the components located behind the electric coil 34 just mentioned, a proximal stator pole shoe is not represented.

The stator 18 of the stereoscopic optical system 10 shown in FIGS. 2 and 3 comprises, at its distal end 36, a distal stator pole shoe 38. At its opposite proximal end 40 in the longitudinal axial direction L, the stator 18 comprises a proximal stator pole shoe 42. In addition, the stator 18 comprises a central stator pole shoe 44 which is arranged between the permanent magnets 30, 32 in the longitudinal axial direction L and is formed, in the exemplary embodiment shown, from a proximal central stator part pole shoe 46 and from a distal central stator part pole shoe 48. An air gap 50 is, for example, provided between the proximal central stator part pole shoe 46 and the distal central stator part pole shoe 48. The coil 34 is divided into a distal coil 52 and a proximal coil 54.

The distal stator pole shoe 38, the distal coil 52, the distal permanent magnet 30 and the distal central stator part pole shoe 48 form a prefabricated distal assembly 60. The proximal central stator part pole shoe 46, the proximal coil 54, the proximal permanent magnet 32 and the proximal stator pole shoe 42 form a proximal assembly 62. The components of the distal assembly 60 are, for example, bonded to one another. The same applies to the components of the proximal assembly 62. Thus, it is possible that prefabricated assemblies 60, 62 are provided and the stereoscopic optical system, more precisely the stator 18 thereof, is composed of these. In connection with this, it is for example provided that the two assemblies 60, 62 are prefabricated in an identical manner. The difference between the distal assembly 60 and the proximal assembly 62 is purely the poling, i.e. the alignment, of the permanent magnets 30, 32 thereof. In order to provide an opposing orientation of the permanent magnets 30, 32 of the two assemblies 60, 62, one of the two assemblies 60, 62 can be installed, rotated by 180° with respect to the other assembly 60, 62.

The permanent magnets 30, 32, which are integrated into the assemblies 60, 62, are for example block-shaped magnets. These are additionally arranged, for example, in multiple groups, wherein the groups can be arranged at positions which are opposite one another. In the represented exemplary embodiment, the permanent magnets 30, 32 are arranged in two groups. The distal permanent magnet thus comprises the magnetic block designated with reference numeral 30 and reference numeral 30'. The proximal permanent magnet 32 comprises the block provided above in the longitudinal axial direction L proximally behind the distal permanent magnet 30 as well as a further magnetic block 32', which is not visible in the figures, which is located proximally behind the distal permanent magnetic block 30' in the longitudinal axial direction L. The permanent magnets 30, 32 are oppositely polarized in the longitudinal axial direction L. This means that the magnetic blocks repel one another. Said repelling force ensures that the distal assembly 60 and the proximal assembly 62 are forced apart such that the air gap 50 remains between them. The distal assembly 60 is pressed against a distal stop, while the proximal assembly 62 is pressed against a proximal stop. The assemblies 60, 62 can be aligned without the position attained being dependent on component tolerances.

It is not necessary for the two assemblies 60, 62 to be bonded to one another in the installation situation. The repelling magnetic forces acting between the assemblies are large enough to keep the assemblies 60, 62 in place. If the assemblies 60, 62 are to be fixed, an adhesive is deployed which shows a small volume shrinkage (for example less than 5 vol.-%) during the curing process.

The groups of the block-shaped permanent magnets are each arranged on a flat side of an arrangement formed from the right and left guide tube 26, 28. FIG. 3 shows such features clearly.

The left guide tube 26 and the right guide tube 28 are accommodated in a joint component 64. As already indicated, the left guide tube 26 and/or the right guide tube 28 can be separate components, for example tubes. It is, however, likewise provided that the left guide tube 26 and/or the right guide tube 28 are inset as bores in the joint component 64. Said joint component 64 has a dumbbell-shaped cross-section in a plane transversely to the longitudinal axial direction L. An inner contour of the pole shoes 38, 48, 46, 42 corresponds to an outer contour of the dumbbell-shaped component 64. An outer contour of the pole shoes 38, 48, 46, 42 is in the form of a circular segment, at least in sections. As FIGS. 2 and 3 show, said sections of the pole shoes 38, 48, 46, 42 are located on the front sides of the arrangement formed from the left and right guide tube 26, 28 and not on the flat sides thereof.

The coil 34, i.e. the distal coil 52 and the proximal coil 54, surround(s) the left and right guide tube 26, 28 and is/are oval in a plane arranged perpendicular to the longitudinal axial direction L. The permanent magnets 30, 32 are arranged on an outer side 66 of the coil 34 facing away from the guide tubes 26, 28. More precisely, the distal permanent magnet 30, 30' is arranged on an outer side 66 of the distal coil 52 and a proximal permanent magnet 32 is arranged on the outer side 66 of a proximal coil 54.

Due to their arrangement, the permanent magnets 30, 32 form magnetic return elements for the electromagnetic field 68 generated by the electric coil 34.

For example, the permanent magnets 30, 30', 32, 32' or only one of these permanent magnets is/are produced from a plastic matrix, in which magnetic particles such as magnetically hard particles, are embedded. Such a permanent magnet can be produced using an injection molding method. During the production of the permanent magnet 30, 30', 32, 32', not only can the permanent magnet itself be produced, but the components of the corresponding assembly 60, 62 can also be connected to one another. Additionally, a coil wire of the coil 34 can be guided through the permanent magnet 30, 30', 32, 32', in other words, the coil wire is also molded.

Figure 4:
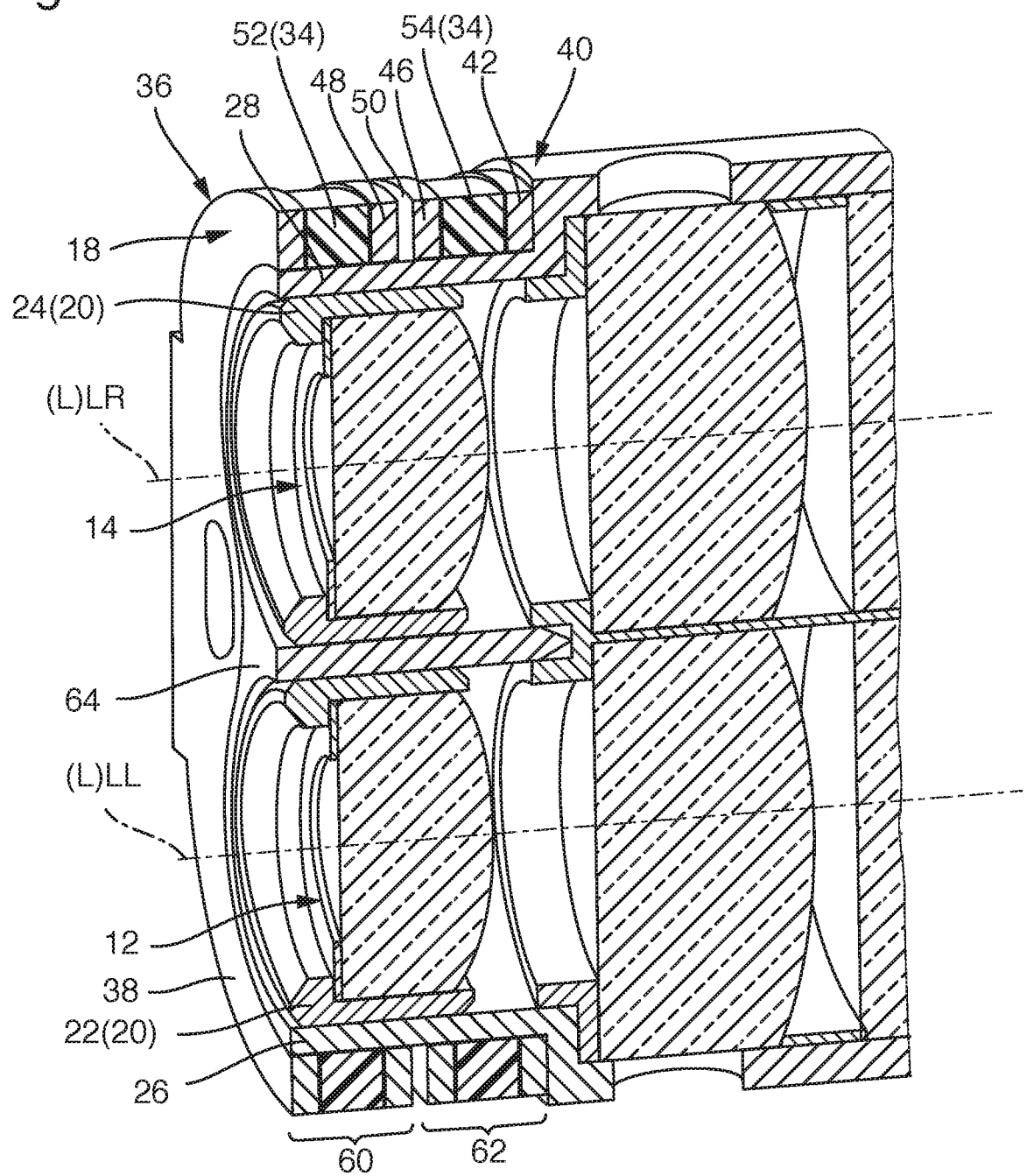

FIG. 4 shows the stereoscopic optical system 10 in a schematically simplified sectional view in a plane, in which a connecting line is located between the two optical channels 12, 14. The longitudinal axial directions LL, LR of the left optical channel 12 and of the right optical channel 14 are also located in this plane.

Figure 5:
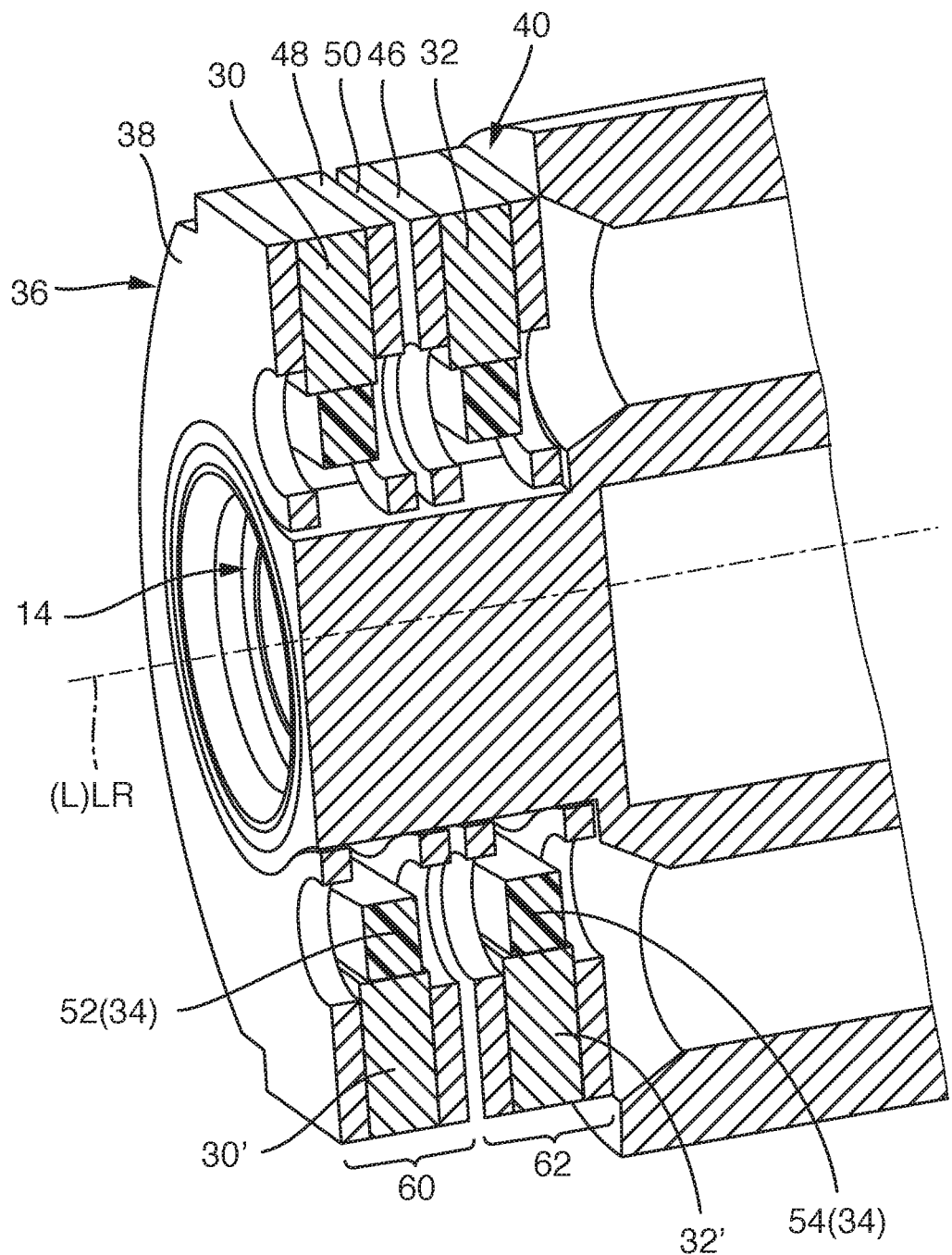
FIG. 5 illustrates a further schematic sectional view in a plane which is located perpendicular to that plane, in which the sectional view represented in FIG. 4 is located, FIGS. 6 and 7 each illustrate a schematically simplified sketch in order to explain the mode of operation of an electromagnetic actuator deployed in a stereoscopic optical system.

FIG. 5 shows a further schematic sectional view in a plane which is located perpendicular to that plane, in which the sectional view represented in FIG. 4 is located.

The mode of operation of the electromagnetic actuator of the stereoscopic optical system 10 is explained below, with reference to the schematically simplified diagrams in FIGS. 6 and 7.

Figure 6:
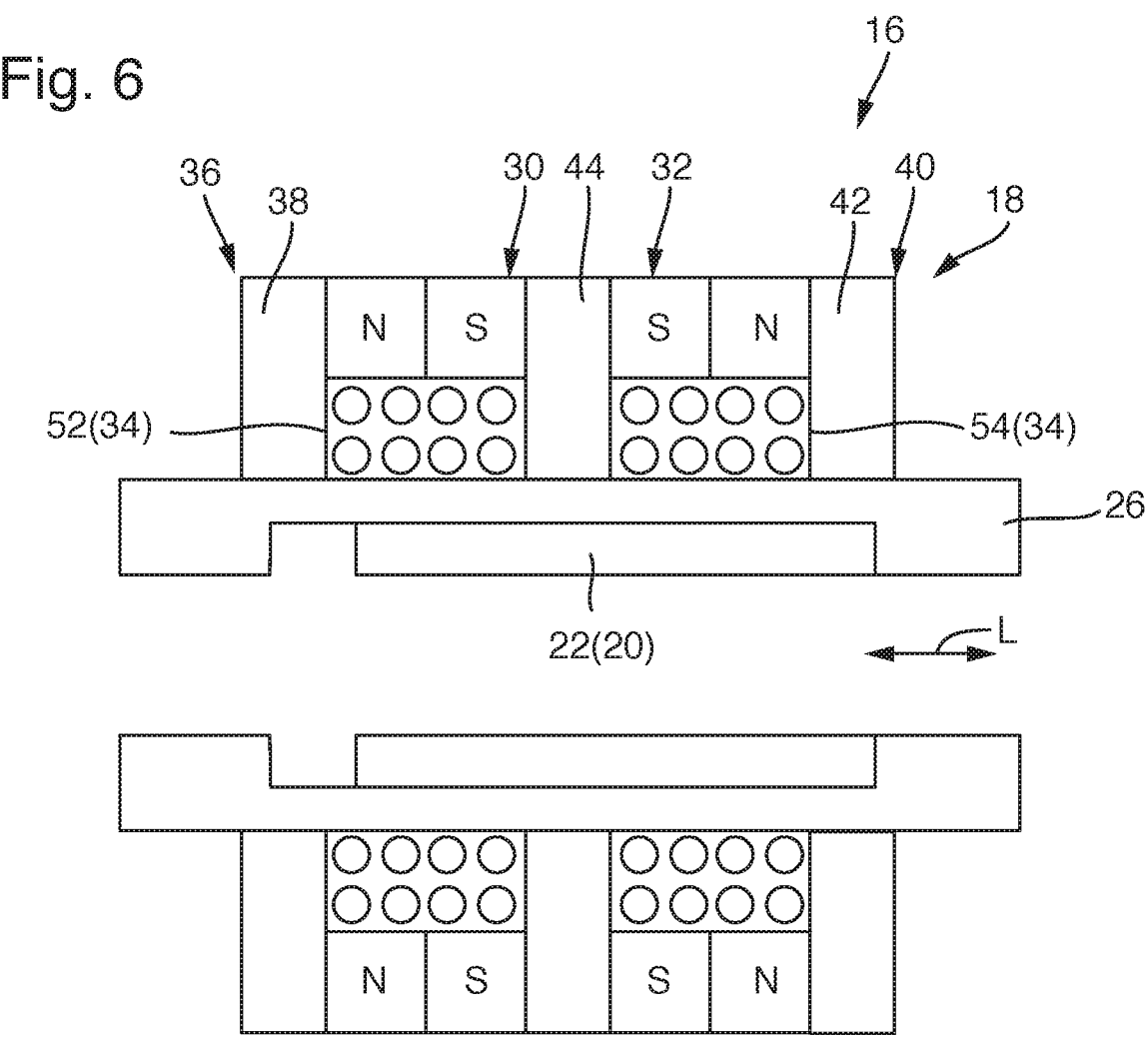

FIG. 6 shows the electromagnetic actuator 16 in a deenergized condition, in which the rotor thereof, which is purely by way of example the left rotor 22, is located in a proximal end position. The rotor 22 is movably accommodated within the left guide tube 26 in the longitudinal axial direction L. The stator 18 of the electromagnetic actuator 16 is located outside the guide tube 26. The distal permanent magnet 30 and the proximal permanent magnet 32, which are oppositely polarized, are additionally represented. The north-south directions of the permanent magnets 30, 32 are located parallel to the longitudinal axial direction L. A distal stator pole shoe 38 is located at a distal end 36 of the stator 18, a proximal stator pole shoe 42 is located at a proximal end 40 of the stator 18. A central stator pole shoe 44 is located between the permanent magnets 30, 32 in the longitudinal axial direction L. The coil 34 comprises a distal coil 52 and a proximal coil 54.

Figure 7:
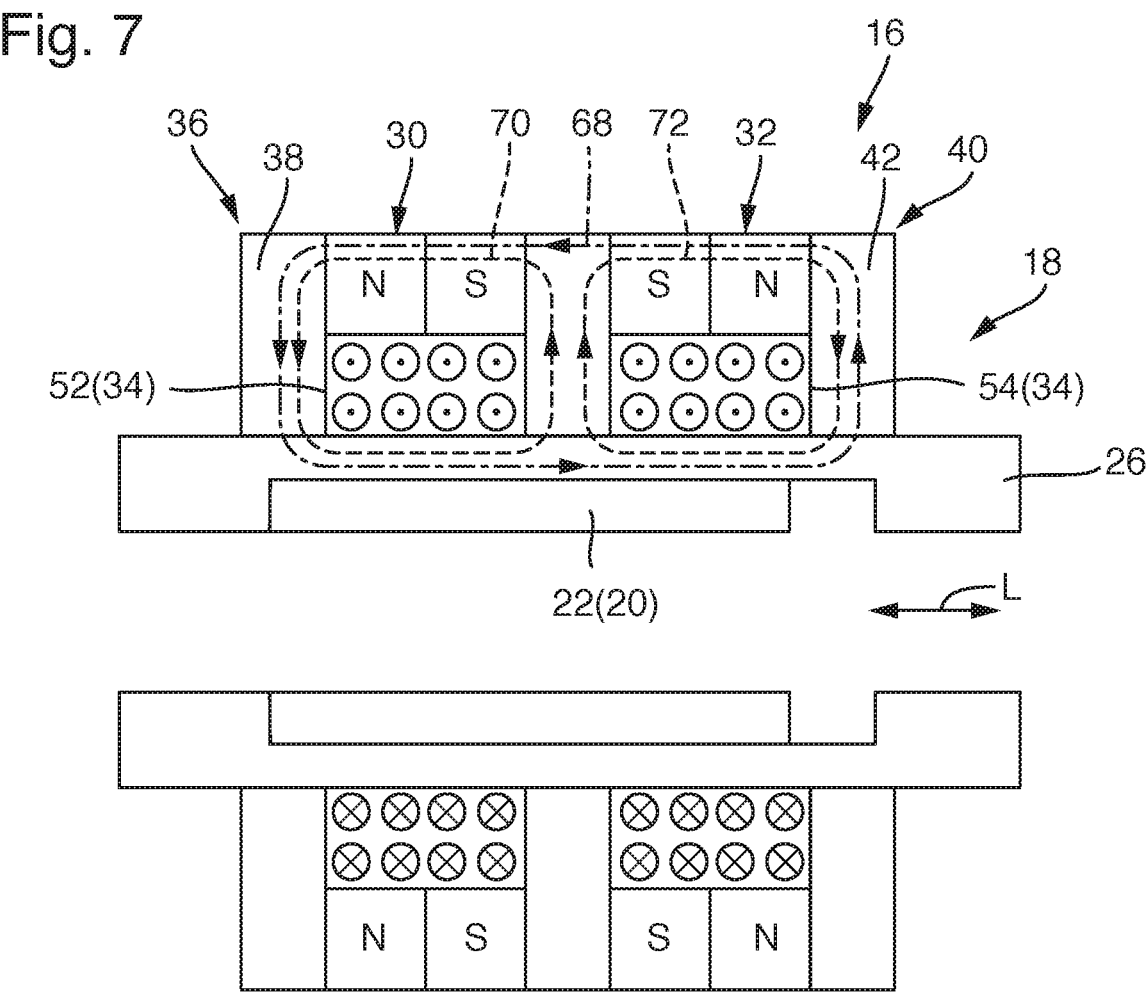

FIG. 7 shows the electromagnetic actuator 16, wherein the distal coil 52 and the proximal coil 54 are energized. The two coils 52, 54 are coupled to one another such that a first magnetic field generated by the respective coil 52, 54 and a second magnetic field are similarly oriented. This is the result of the identical energizing of the two coils 52, 54. The current flow direction is indicated in the schematically sketched conductors of the coils 52, 54. A current direction pointing out of the drawing plane is indicated by a dot and a current direction directed into the drawing plane is indicated by a cross. The first and the second magnetic field of the coils 52, 54 add up to produce the electromagnetic field 68 which is represented in a dot-dashed manner line.

The electromagnetic field 68 superimposes a first static magnetic field 70 which is generated by the distal permanent magnet 30 and a second static magnetic field 72 which is generated by the second permanent magnet 32. At the distal end 36 of the stator 18, the electromagnetic field 68 and the first static magnetic field 70 are constructively superimposed such that a reinforcement of the total magnetic field present occurs due to the energizing of the coil 34 on this side of the stator 18. At the proximal end 40 of the stator 18, the electromagnetic field 68 and the second static magnetic field 72, which is generated by the proximal permanent magnet 32, are in the opposite direction such that an attenuation of the total magnetic field present takes place at this end of the stator 18. Thus, a greater force acts in a gap (which is closed in the represented situation) between the rotor 22 and the guide tube 26 at the distal end 36 than at the proximal end 40, such that the rotor 20 is displaced into the end position shown in FIG. 7. A displacement back into the starting position is effected by energizing the coil 34 accordingly in the opposite direction.

The corresponding components are purely represented in the upper half of the drawing in FIGS. 6 and 7. The represented sectional view is, however, rotationally symmetrical to a central longitudinal axis, which is why the corresponding components can also be similarly found in the lower half of the respective drawing.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

2 Endoscope
4 Endoscope shaft
6 Distal end
8 Handle
10 Stereoscopic optical system
12 Left optical channel
14 Right optical channel
16 Electromagnetic actuator
18 Stator
20 Rotor
22 Left rotor
24 Right rotor
26 Left guide tube
28 Right guide tube
30, 30' Distal permanent magnet
32, 32' Proximal permanent magnet
34 Coil
36 Distal end of the stator
38 Distal stator pole shoe
40 Proximal end of the stator
42 Proximal stator pole shoe
44 Central stator pole shoe
46 Proximal central stator part pole shoe
48 Distal central stator part pole shoe
50 Air gap
52 Distal coil
54 Proximal coil
60 Distal assembly
62 Proximal assembly
64 Dumbbell-shaped component
66 Outer side
68 Electromagnetic field
70 First static magnetic field
72 Second static magnetic field
L Longitudinal axial direction
LL Left longitudinal axial direction
LR Right longitudinal axial direction

What is claimed is:

1. A stereoscopic optical system for use with a surgical instrument, the stereoscopic optical system comprising:
a left optical channel;
a right optical channel; and
an electromagnetic actuator comprising a stator and a rotor;
wherein first optical components of the left optical channel are arranged in a left guide tube and second optical components of the right optical channel are arranged in a separate right guide tube;
the stator is arranged outside the left guide tube and the right guide tube;
the rotor comprises a left rotor, in which at least one of the first optical components of the left optical channel is accommodated, and a right rotor, in which at least one of the second optical components of the right optical channel is accommodated;
the left rotor and the right rotor are mounted in a respective one of the left guide tube and the right guide tube such that the left rotor and the right rotor are movable in a longitudinal axial direction of the left guide tube and the right guide tube;
the left rotor and the right rotor each at least partially comprise one of a paramagnetic and a ferromagnetic material and are movable in the longitudinal axial direction by application of an electromagnetic field;
the stator comprises a distal permanent magnet and a proximal permanent magnet which are oppositely polarized in the longitudinal axial direction;
the stator comprises an electric coil for generating the electromagnet field; and
the electric coil surrounds the left guide tube and the right guide tube.

2. The stereoscopic optical system according to claim 1, wherein:
a distal end of the stator is formed by a distal stator pole shoe and an opposite proximal end in the longitudinal axial direction is formed by a proximal stator pole shoe;
the stator further comprises a central stator pole shoe arranged between the distal permanent magnet and the proximal permanent magnet in the longitudinal axial direction; and the central stator pole shoe is formed from a proximal central stator part pole shoe and from a distal central stator part pole shoe.

3. The stereoscopic optical system according to claim 2, wherein:
the electric coil comprises a distal coil and a proximal coil;
the distal stator pole shoe, the distal coil, the distal permanent magnet and the distal central stator part pole shoe form a prefabricated distal assembly; and
the proximal central stator part pole shoe, the proximal coil, the proximal permanent magnet and the proximal stator pole shoe form a prefabricated proximal assembly.

4. The stereoscopic optical system according to claim 3, wherein one or more of the distal stator pole shoe, the distal coil, the distal permanent magnet and the distal central stator part pole shoe of the prefabricated distal assembly are bonded together and the proximal central stator part pole shoe, the proximal coil, the proximal permanent magnet and the proximal stator pole shoe of the prefabricated proximal assembly are bonded together.

5. The stereoscopic optical system according to claim 2, wherein:
the left guide tube and the right guide tube are accommodated in a joint component which has a dumbbell-shaped cross-section in a plane transverse to the longitudinal axial direction; and
wherein an inner contour of the distal stator pole shoe, the proximal stator pole shoe, the distal central stator part pole shoe and the proximal central stator part pole shoe correspond to an outer contour of the dumbbell-shaped component and an outer contour of the distal stator pole shoe, the proximal stator pole shoe, the distal central stator part pole shoe and the proximal central stator part pole is in the form of a circular segment at least in sections.

6. The stereoscopic optical system according to claim 1, wherein the electric coil is oval in a plane oriented perpendicular to the longitudinal axial direction.

7. The stereoscopic optical system according to claim 1, wherein the distal permanent magnet and the proximal permanent magnet are arranged on an outer side of the electric coil facing away from the guide tubes.

8. The stereoscopic optical system according to claim 1, wherein the distal permanent magnet and the proximal permanent magnet are block-shaped magnets which are arranged in two groups, wherein the two groups are arranged opposite one another on a flat side each of an arrangement formed from the left guide tube and the right guide tube.

9. The stereoscopic optical system according to claim 1, wherein the distal permanent magnet and the proximal permanent magnet form magnetic return elements for the magnetic field generated by the electric coil.

10. The stereoscopic optical system according to claim 1, wherein at least one of the distal permanent magnet and the proximal permanent magnet comprises magnetically hard particles which are embedded in a plastic matrix.

11. The stereoscopic optical system according to claim 10, wherein at least one coil wire of the electric coil is molded in at least one of the distal permanent magnet and the proximal permanent magnet.

12. A surgical instrument comprising:
the left guide tube and the right guide tube; and
the stereoscopic optical system according to claim 1.

13. The surgical instrument according to claim 12, wherein the left guide tube and the right guide tube are provided in an insertion section of an endoscope.

* * * * *